(12) United States Patent
Deisinger et al.

(10) Patent No.: US 10,835,421 B2
(45) Date of Patent: Nov. 17, 2020

(54) PATIENT ADAPTER FOR AN EYE LASER APPARATUS

(71) Applicant: Wavelight GmbH, Erlangen (DE)

(72) Inventors: Thomas Deisinger, Erlangen (DE); Daniel Thimm, Erlangen (DE)

(73) Assignee: Alcon Inc. (CH)

( * ) Notice: Subject to any disclaimer, the term of this patent is extended or adjusted under 35 U.S.C. 154(b) by 458 days.

(21) Appl. No.: 15/091,156

(22) Filed: Apr. 5, 2016

(65) Prior Publication Data

US 2016/0331586 A1 Nov. 17, 2016

(30) Foreign Application Priority Data

May 15, 2015 (EP) .................................... 15001469

(51) Int. Cl.
*A61F 9/009* (2006.01)
*A61F 9/008* (2006.01)

(52) U.S. Cl.
CPC .......... *A61F 9/009* (2013.01); *A61F 9/00827* (2013.01)

(58) Field of Classification Search
CPC ... A61F 9/00825; A61F 9/009; A61F 9/00827
USPC .............................................................. 606/5
See application file for complete search history.

(56) References Cited

U.S. PATENT DOCUMENTS

| | | | | |
|---|---|---|---|---|
| 2002/0103482 A1* | 8/2002 | Scholler | ................... | A61F 9/009 606/5 |
| 2007/0237620 A1* | 10/2007 | Muhlhoff | ................ | A61F 9/009 414/751.1 |
| 2008/0287927 A1 | 11/2008 | Rathjen | | |
| 2011/0022035 A1 | 1/2011 | Porter | | |
| 2011/0190741 A1 | 8/2011 | Deisinger | | |
| 2014/0276673 A1* | 9/2014 | Heitel | ..................... | A61F 9/009 606/4 |
| 2015/0088175 A1* | 3/2015 | McWhirter | ............. | A61F 9/009 606/166 |

(Continued)

FOREIGN PATENT DOCUMENTS

| | | |
|---|---|---|
| CN | 102143725 A | 8/2011 |
| EP | 1970034 A1 | 9/2008 |

(Continued)

OTHER PUBLICATIONS

European Search Report; EP Application No. 15001469; dated Nov. 12, 2015; 9 pages.

*Primary Examiner* — Lynsey C Eiseman
*Assistant Examiner* — Amanda L. Steinberg

(57) ABSTRACT

A patient adapter for an eye laser apparatus comprises a first partial adapter unit, including a suction ring portion to be placed on an eye and affixed on the eye by means of suction force, the suction ring portion having a ring axis; and a second partial adapter unit formed separately from the first partial adapter unit, the second partial adapter unit being configured for releasable coupling to the eye laser apparatus and including an eye contact element for shaping the surface of the eye, wherein the two partial adapter units are held together mechanically in a module between a first relative position, in which the eye contact element has a first axial position with respect to the suction ring portion, and a second relative position, in which the eye contact element has a second axial position with respect to the suction ring portion.

11 Claims, 12 Drawing Sheets

(56) References Cited

U.S. PATENT DOCUMENTS

2015/0190277 A1\* 7/2015 Gooding ............ A61F 9/00802
606/6

FOREIGN PATENT DOCUMENTS

| EP | 2456402 B1 \* | 8/2014 | ............ A61F 9/009 |
| JP | 2013248303 A | 12/2013 | |
| WO | 2010/022745 A1 | 3/2010 | |
| WO | 2012/041347 A1 | 4/2012 | |

\* cited by examiner

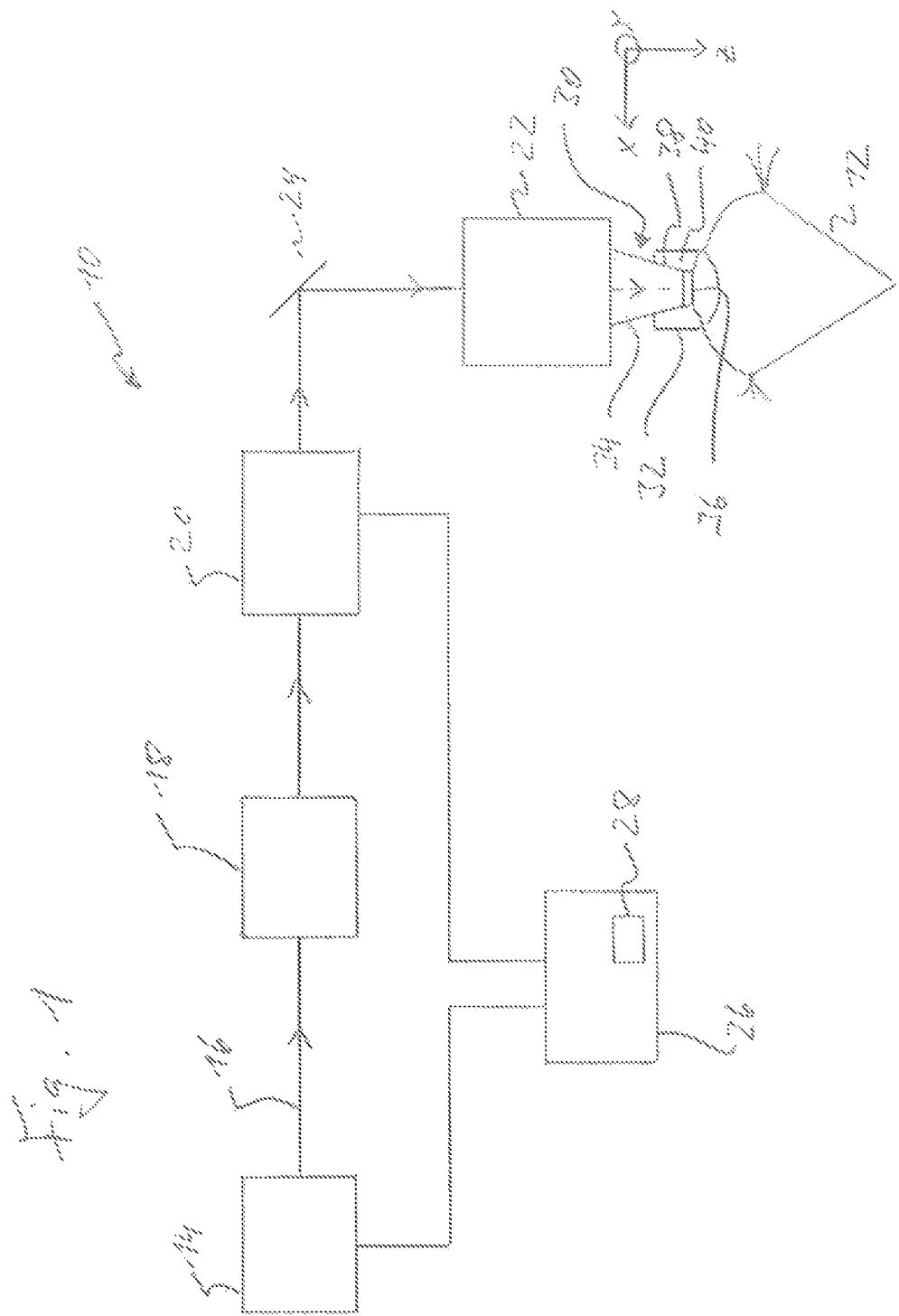

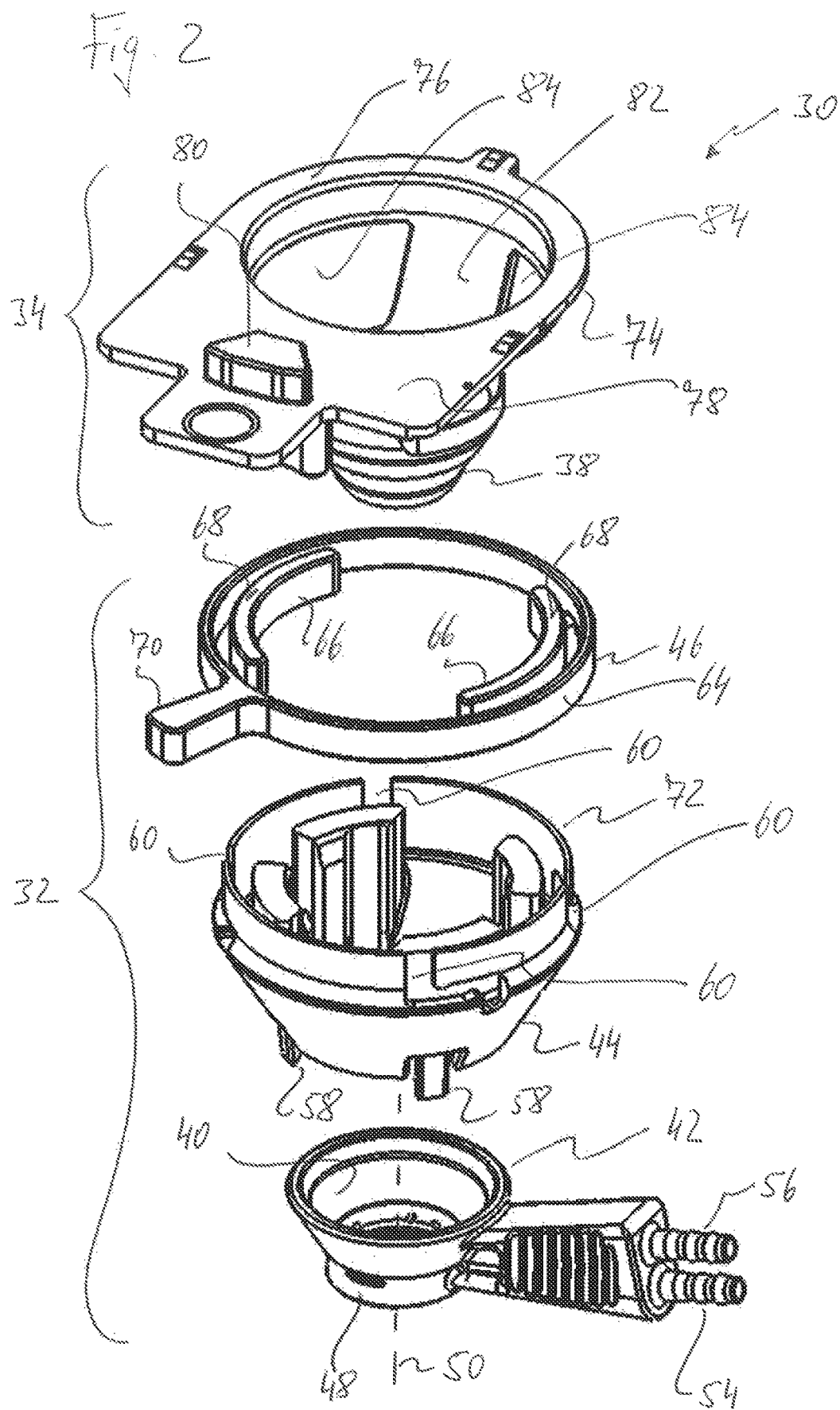

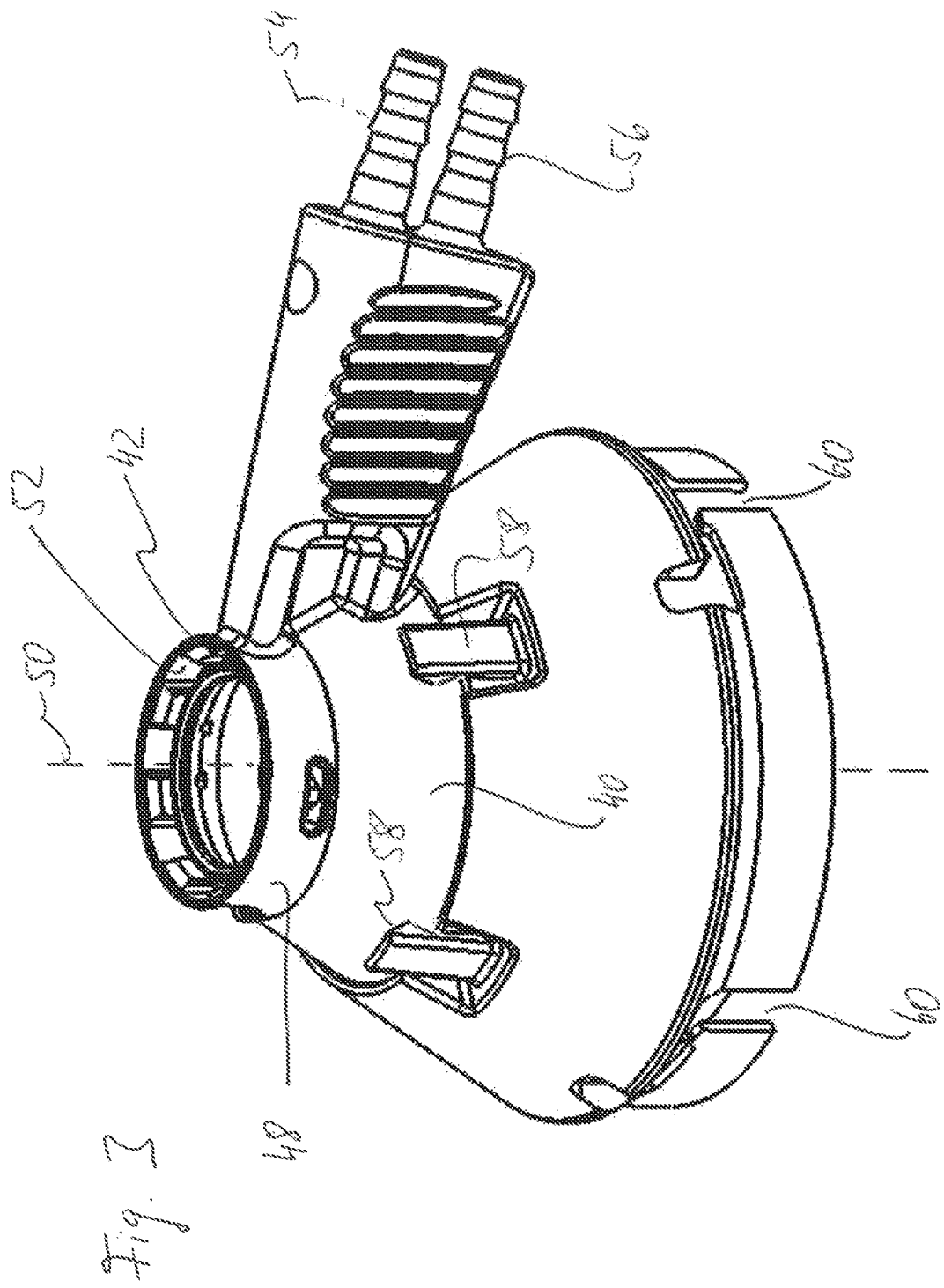

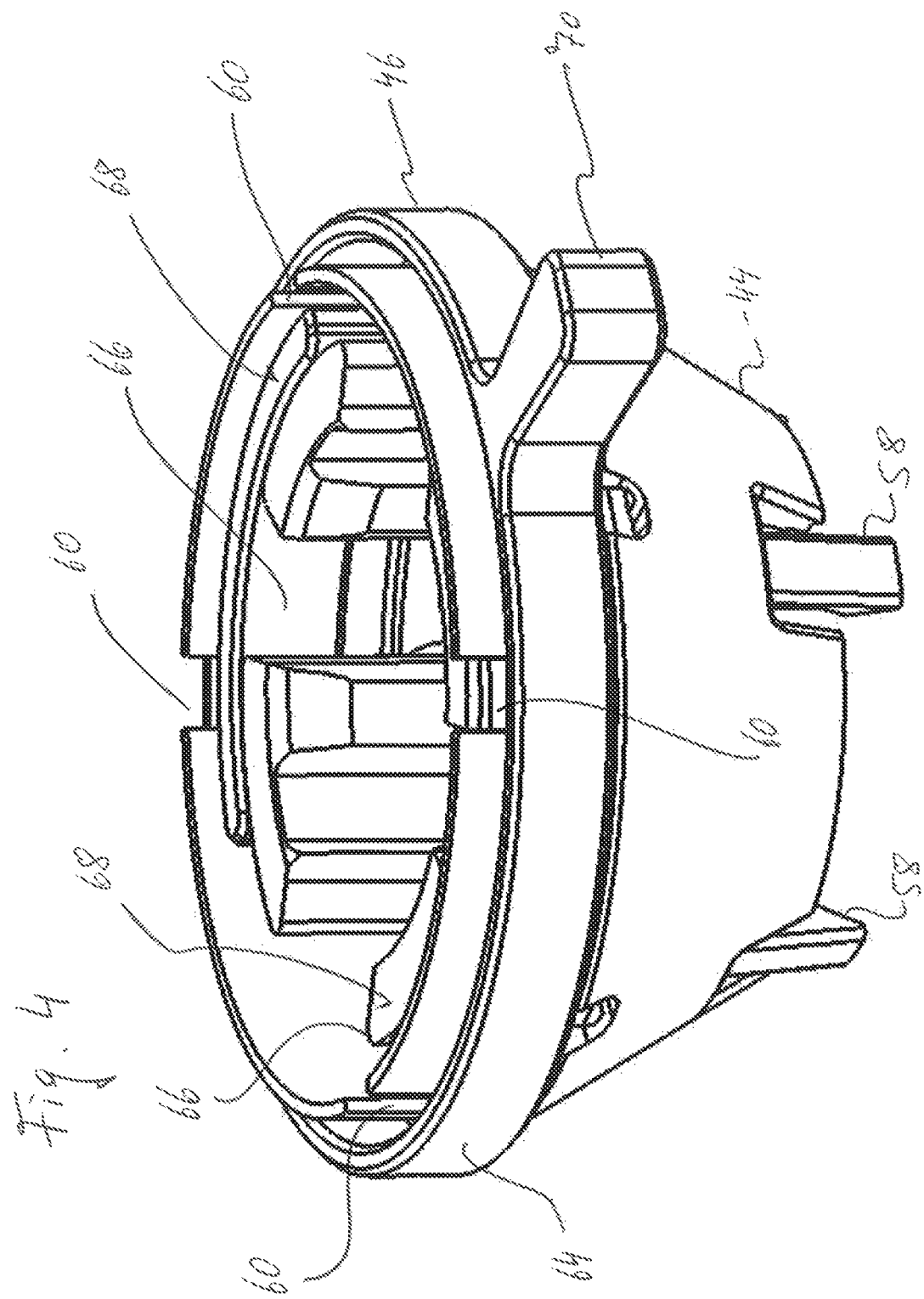

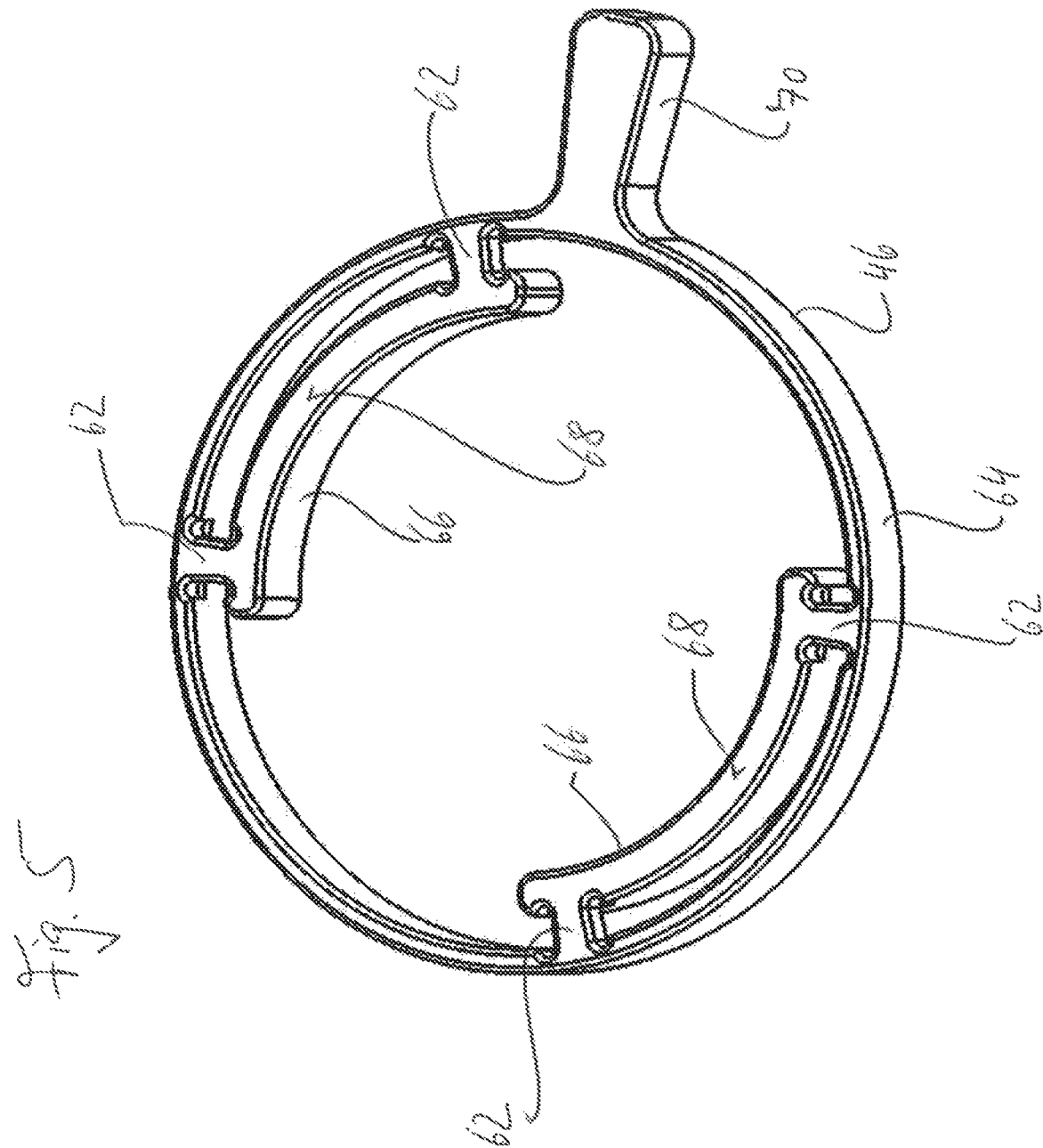

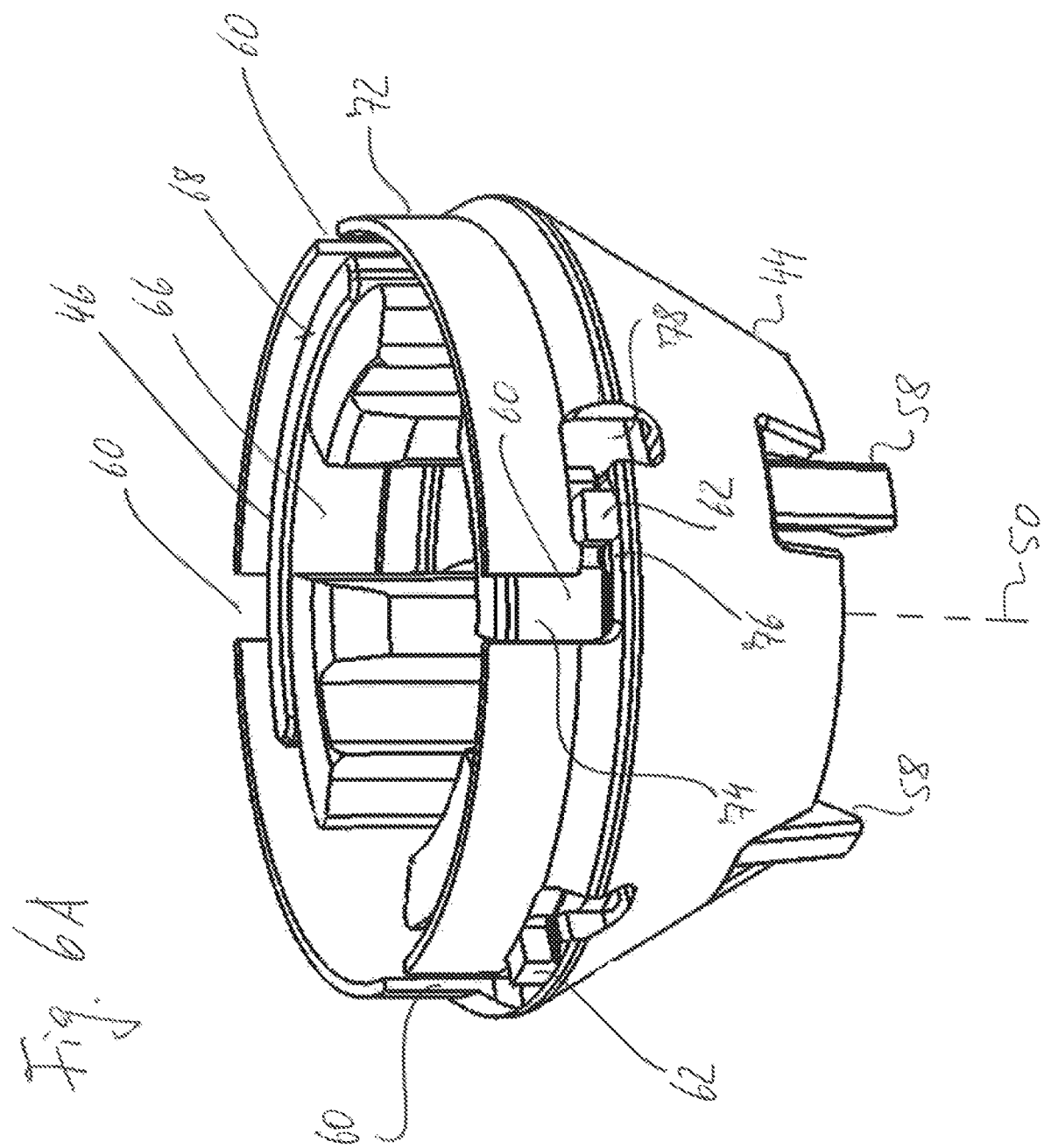

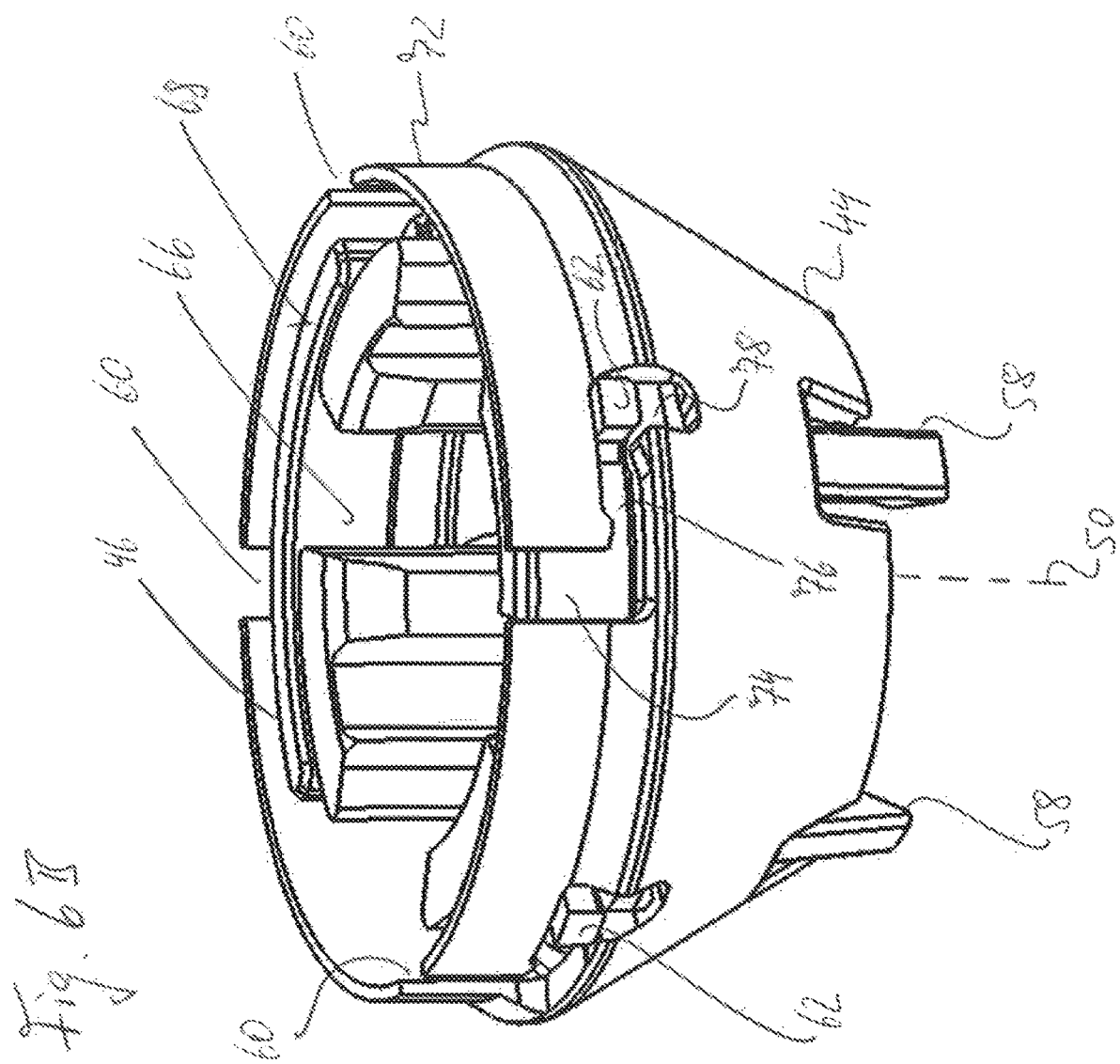

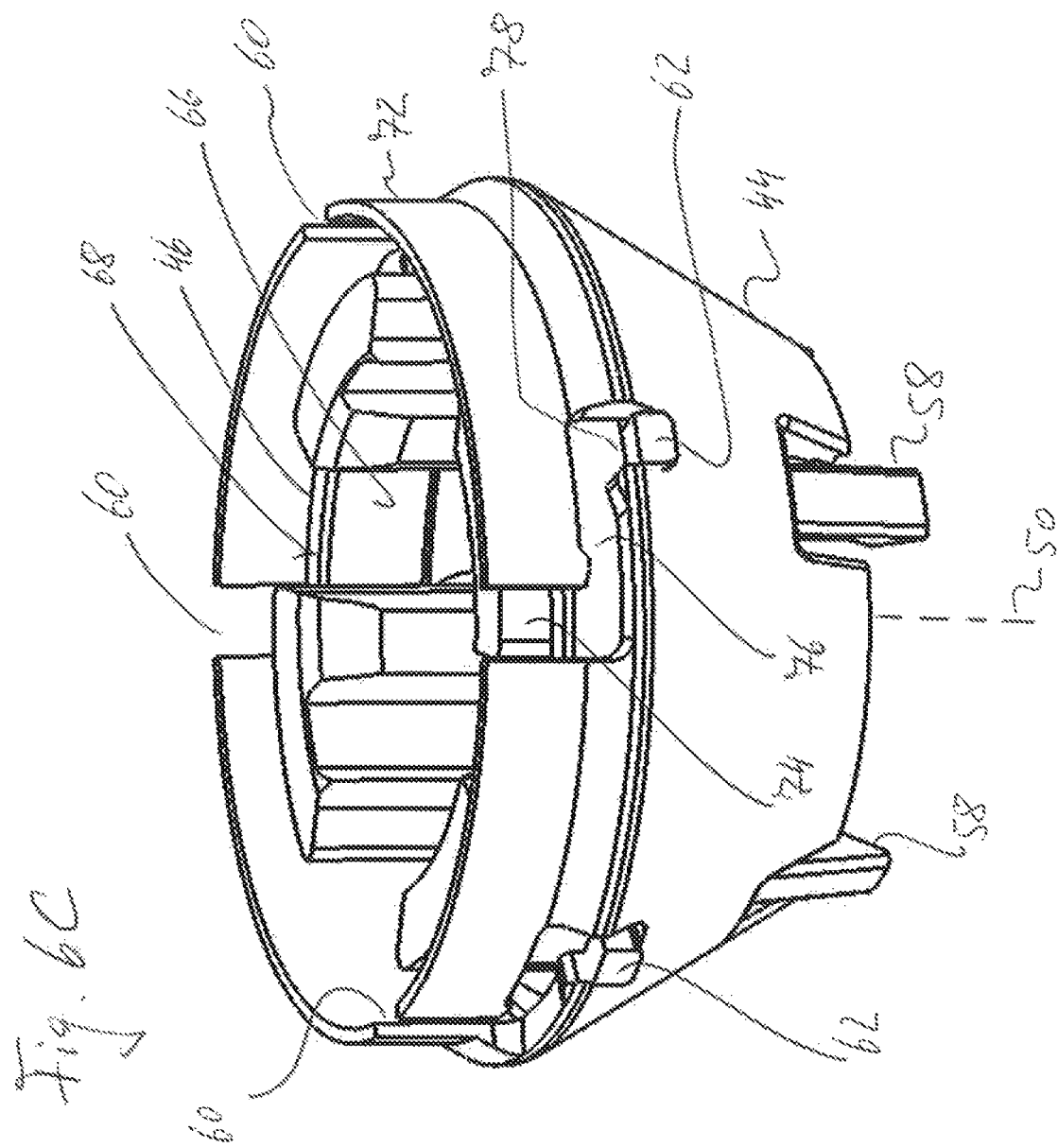

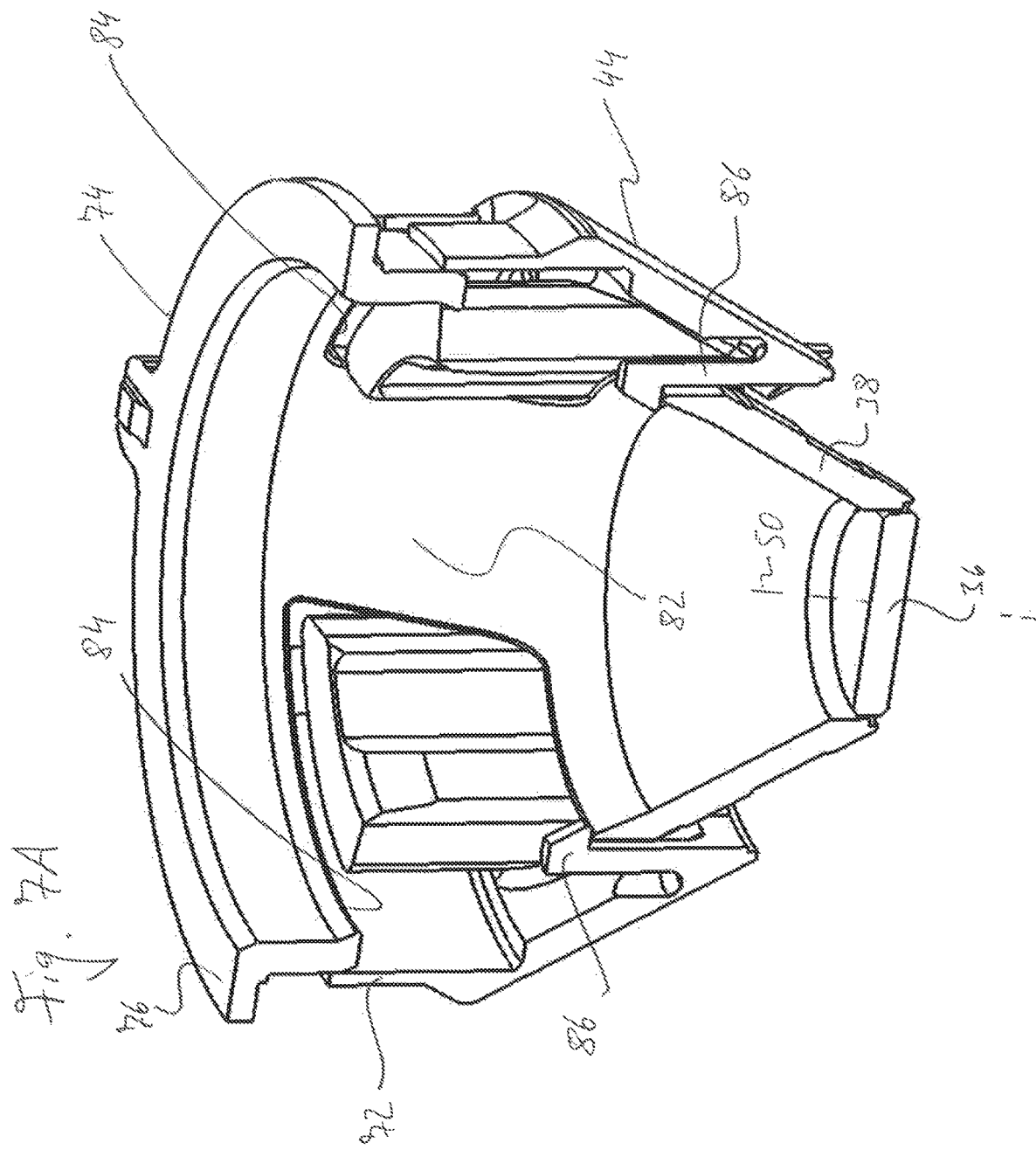

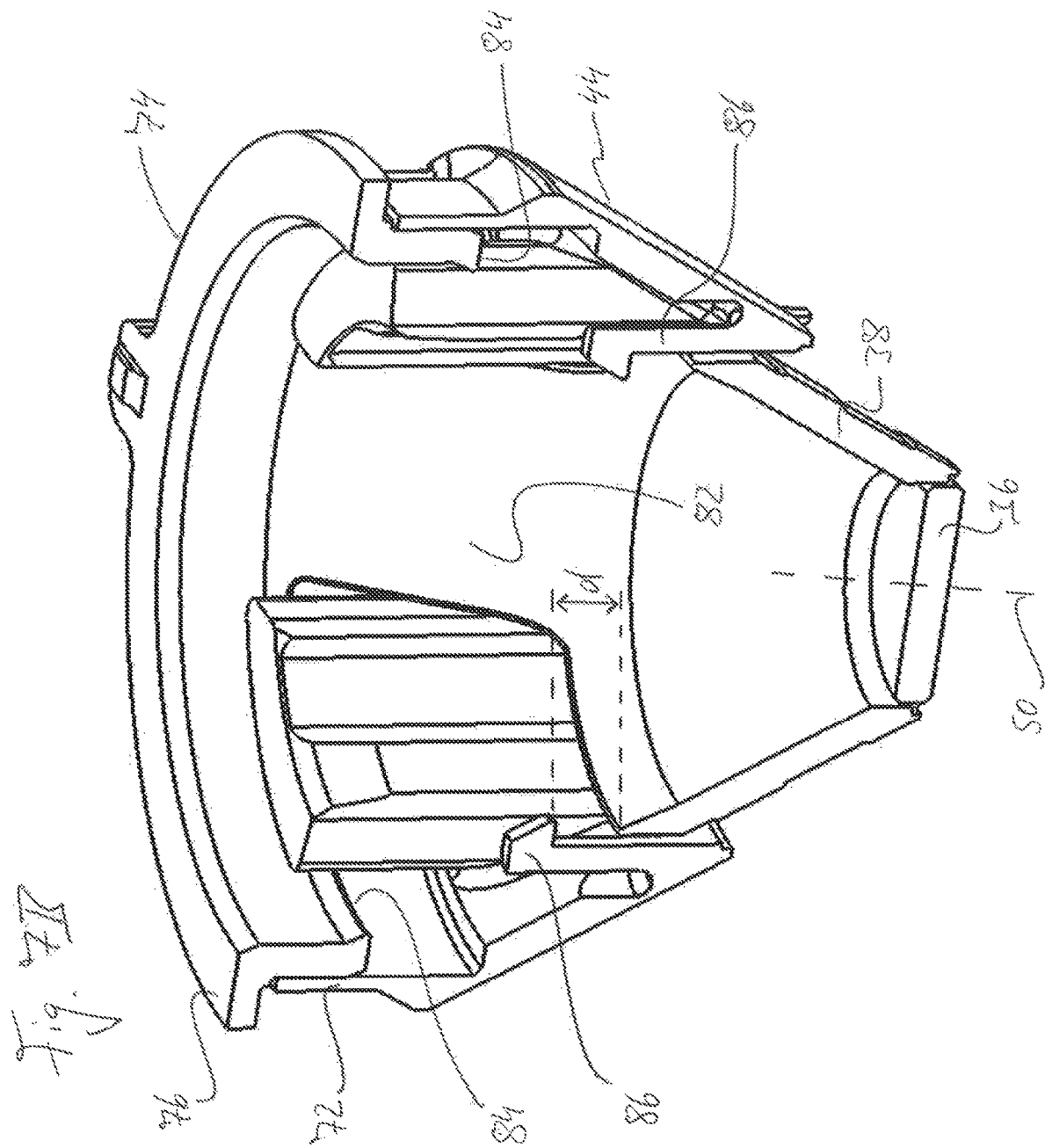

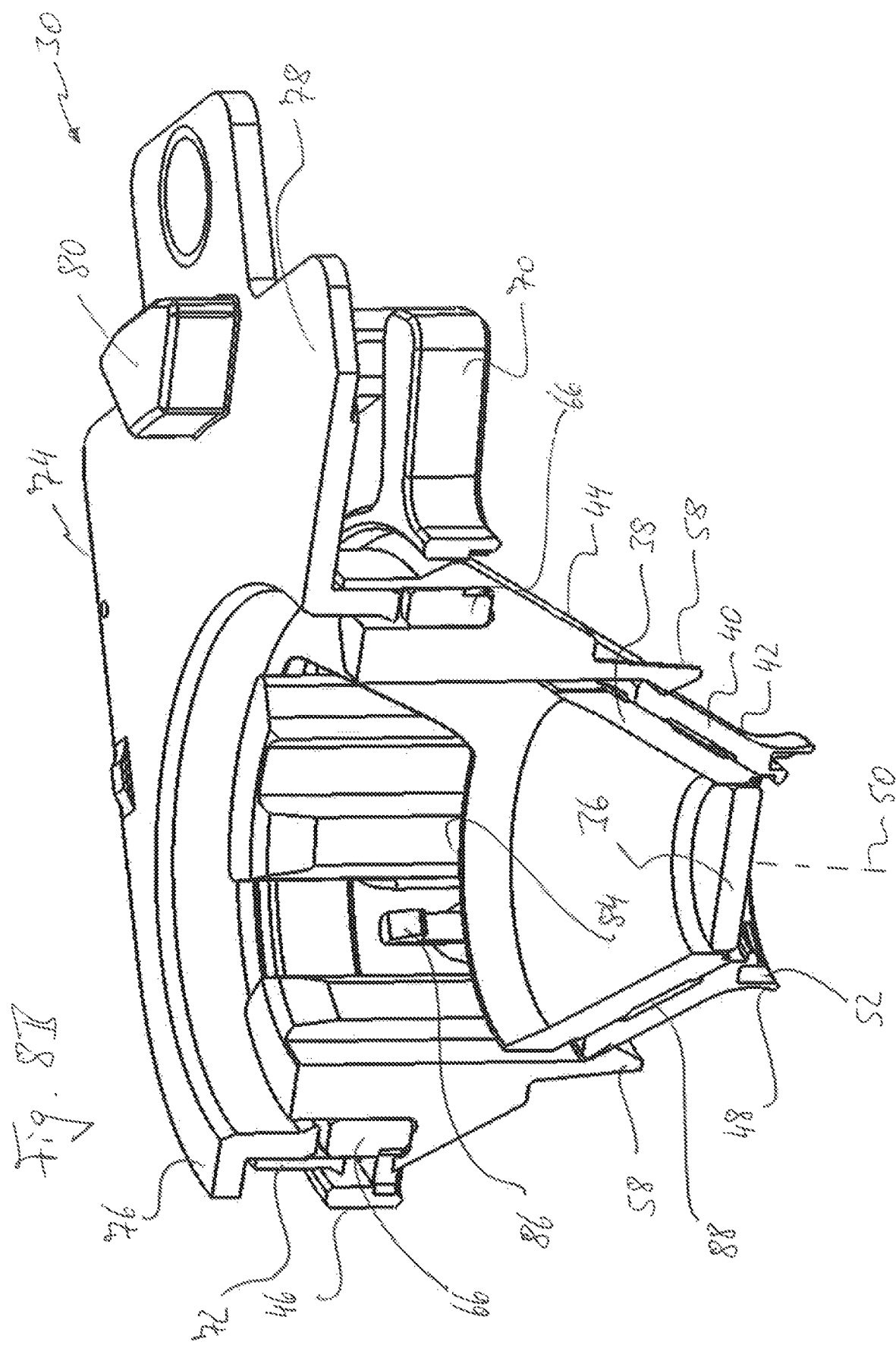

PATIENT ADAPTER FOR AN EYE LASER APPARATUS

CROSS REFERENCE TO RELATED APPLICATIONS

This application claims priority to European Patent Application Serial Number 15001469.4, filed 15 May 2015, titled "PATIENT ADAPTER FOR AN EYE LASER APPARATUS," which is hereby incorporated by reference in its entirety.

TECHNICAL FIELD

The present invention relates to a patient adapter for an eye laser apparatus.

BACKGROUND

A patient adapter makes it possible to mechanically couple an eye to be treated to an eye laser apparatus. In this way, the eye can be positioned accurately with respect to the laser apparatus in the direction of propagation of the laser beam emitted by the laser apparatus (this direction is often referred to as z-direction). In a laser treatment of the eye with the goal of making an incision (cut) in the eye by means of the laser beam, it is important to know the z-position of the eye in a coordinate system of the laser apparatus. The patient adapter makes it possible to secure the eye in relation to the laser apparatus in the z-direction and thus creates a prerequisite for an accurate application of the incision in the eye in the z-direction.

A conventional example of a patient adapter is designed in two parts and comprises a suction ring, which is placed on the eye and affixed there by suction force, as well as a conical spacer, which can be connected to the laser apparatus and has an applanation plate that is transmissive for laser radiation in the region of a narrow cone end, where the plate has a contact surface for the eye. First, the suction ring is placed on the eye by the surgeon and is affixed there by applying a vacuum. The spacer is in turn mounted on the laser apparatus. In this phase, the suction ring and the spacer are still completely separate from one another. Next, there is a relative approach of the eye with the suction ring sitting on it, on the one hand, and the spacer, which is held on the laser apparatus, on the other hand, until the spacer enters an insertion funnel formed on the suction ring. Finally, another vacuum is created to draw the spacer axially against the suction ring. The insertion funnel of the suction ring ensures a radial centering of the suction ring in relation to the spacer. After bringing the spacer closer to the suction ring by suction, the surface of the eye is leveled off by the applanation plate. In this condition, a cut can be made in the eye tissue, for example, in the cornea, by means of the laser beam of the laser apparatus.

This conventional solution is sufficient if the cut to be created by laser technology (or in general: the shape of the cut to be created) should not itself cause any change in the refractive properties of the eye. For example, this is the case in a LASIK treatment (LASIK: laser in-situ keratomileusis), wherein first, by means of a laser beam, a corneal segment on the surface of the eye, which is referred to as a "flap" in the English jargon, is cut open. This segment is then folded over to the side to expose the underlying corneal tissue for a subsequent laser ablation. The cut to prepare the flap by itself does not provide any refraction correction. The goal of a refractive correction is pursued only by removal of stromal tissue by laser ablation.

SUMMARY OF THE DISCLOSURE

However, there are also laser surgical procedures for making refractive corrections in the eye, in which the cutting pattern created in the eye should manifest a refractive effect immediately. One example is intracorneal lenticular extraction, in which a volume of lenticular tissue is excised by making a posterior cut and an anterior cut in the cornea of the eye and then removing the lenticular tissue through an extraction channel. The cavity formed in the cornea as a result of removing this tissue portion causes the area of corneal tissue in front (i.e., in the anterior direction) to collapse into it and thereby alter the refractive properties of the cornea. The position and shape of the corneal tissue portion to be extracted must always be determined individually for each patient. This means that the cuts required for preparation of the corneal lenticule must be created accurately with respect to a reference axis of the eye (for example, the optical axis or visual axis) in the patient's eye. This requires the reference axis of the eye to be aligned in relation to an optical axis of the laser apparatus. To do so, the patient may be instructed to stare at a fixed light, for example, with the eye to be treated. However, the conventional patient adapter is not suitable for this measure because, when the suction ring is placed on the eye, the reference axis of the eye cannot be aligned with the help of a fixation light.

Therefore, one object of embodiments of the present invention is to provide a patient adapter, which is suitable for performing such surgical methods, in which it is necessary to align a reference axis of an eye to be treated in relation to an optical axis of an eye laser apparatus.

In this regard, an embodiment of the invention makes available a patient adapter for an eye laser apparatus, comprising: a first partial adapter unit including a suction ring portion to be placed on an eye and to be affixed to the eye by suction force, the suction ring portion having a ring axis; and a second partial adapter unit formed separately from the first partial adapter unit, the second partial adapter unit designed for releasable coupling to the eye laser apparatus and including an eye contact element for shaping the surface of the eye, wherein the two partial adapter units are held together mechanically in a module and can be displaced in relation to one another in the module between a first relative position, in which the eye contact element assumes a first axial position in relation to the suction ring portion, and a second relative position, in which the eye contact element assumes a second axial position in relation to the suction ring portion.

In a solution according to the invention, the two partial adapter units may be mounted together as a module on the laser apparatus. This makes it possible to emit a fixating beam of light along the ring axis through the eye contact element and the suction ring portion. While the patient with his eye is brought closer to the module (consisting of the first partial adapter unit and the second partial adapter unit) mounted on the laser apparatus, the patient can align his eye with the fixating beam of light. As soon as the eye comes in contact with the suction ring portion, the suction ring portion can be affixed on the eye by creating a vacuum. Good alignment of the eye with an optical axis of the laser apparatus can be achieved in this way. Next, the two partial adapter units are transferred from the first relative position to the second relative position. This creates a displacement of the eye contact element in the axial direction. This axial displacement (from the first axial position to the second axial position) causes a deformation of the surface of the eye into the desired shaped condition.

In one embodiment of the patient adapter, the first axial position of the eye contact element corresponds to a position in which the eye contact element is still out of contact with the eye when the suction ring portion is placed on the eye. However, the second axial position of the eye contact element corresponds to a position in which the eye contact element is in contact with the eye for shaping it when the suction ring portion is placed on the eye.

In certain embodiments, an arrangement of one or more snap-in tongues is arranged on at least one of the partial adapter units, these snap-in tongues being designed for axial snap-in coupling of the two partial adapter units to one another with an axial clearance.

In certain embodiments, one of the two partial adapter units is designed with an axially displaceable abutment face for axial stopping of the other partial adapter unit. The patient adapter comprises a control member, which is adjustable between a first control position and a second control position, such that, in the first control position, it suppresses axial displacement of the abutment face, and in the second control position, it allows axial displacement of the abutment face. The abutment face is arranged on the first partial adapter unit, for example.

In embodiments of the invention, the control member is formed by a control ring arranged to rotate about the ring axis, wherein the abutment face is formed by an end face of this control ring facing axially. The control ring is in turn adjustable between a first rotational position, in which it is arranged without any axial clearance in relation to the suction ring portion, and a second rotational position, in which it has axial play in relation to the suction ring portion.

The first rotational position of the control ring corresponds, for example, to an axial position of the eye contact element, in which the eye contact element is still out of contact with the eye when the suction ring portion is placed on the eye. In the second rotational position of the control ring, for example, the axial play allows the control ring to move into an axial position, which corresponds to an axial position of the eye contact element, in which this element is in shaping contact with the eye when the suction ring portion is placed on the eye.

The control ring may have a guided member which is guided in a guide recess in one of the two partial adapter units (for example, the first partial adapter unit). Engagement of the guided element in the guide recess is without clearance in the first rotational position of the control ring, whereas in the second rotational position it is with an axial clearance.

For ease of handling, the control ring may have a radially protruding gripping protrusion for a manual rotational activation of the control ring.

In certain embodiments the first partial adapter unit comprises a suction ring member forming the suction ring portion as well as an auxiliary member, which is designed separately from the former, wherein the auxiliary member is coupled to the suction ring member, and the control member is guided on the auxiliary member in a manner adjustable in relation to the auxiliary member.

For mutual connection of the suction ring member and the auxiliary member, an arrangement of one or more snap-in tongues may be provided on at least one of the suction ring member and the auxiliary member so that the auxiliary member is connected to the suction ring member with axial clearance.

In certain embodiments, the first partial adapter unit has a centering portion, which tapers in the form of a funnel in the axial direction to the suction ring portion. The second partial adapter unit has a conical portion, which is provided for axial insertion into the centering portion. In the second relative position of the two partial adapter units, the conical portion is inserted farther into the centering portion than in the first relative position.

The patient adapter may comprise a suction chamber which is delimited at least partially by the two partial adapter units, by evacuation of which the eye contact element can be held in the second axial position in relation to the suction ring portion. The suction chamber is formed between the centering portion and the conical portion, for example.

In certain embodiments, the one of the first and second partial adapter units (for example, the first partial adapter unit) is designed with a plurality of abutment faces, which are arranged so that they are distributed in the circumferential direction around the ring axis, for axial abutment of the other one of the first and second partial adapter units. Each of these abutment faces is arranged so that it is axially displaceable, wherein the control member, in the first control position, suppresses an axial displacement of each abutment face and, in the second control position, permits an axial displacement of each abutment face.

According to another aspect, embodiments of the present invention provides a method for coupling an eye with an eye laser apparatus, comprising at least the following steps: providing a patient adapter, comprising a first partial adapter unit and a second partial adapter unit designed separately from the first partial adapter unit, wherein the first partial adapter unit has a suction ring portion having a ring axis, wherein the second partial adapter unit is designed for releasable coupling with the eye laser apparatus and has an eye contact element, wherein the first and second partial adapter units are held together mechanically in a module and can be displaced in the module in relation to one another between a first relative position, in which the eye contact element assumes a first axial position in relation to the suction ring portion, and a second relative position, in which the eye contact element assumes a second axial position in relation to the suction ring portion; approaching and aligning the suction ring portion in relation to the eye and then affixing the suction ring portion to the eye by suction force while the second partial adapter unit is coupled to the eye laser apparatus and the two partial adapter units are in the first relative position; and transferring the two partial adapter units from the first relative position into the second relative position to establish or expand a shaping contact of the eye contact element with the eye. It is preferable if the eye contact element is still out of contact with the eye in the first relative position. However, within the scope of the invention, the possibility cannot be ruled out that there is already comparatively minor contact between the eye contact element and the eye in the first relative position.

In certain embodiments, the step of transferring comprises: manipulating a control member to transfer an abutment face for axial stopping of the other one of the two partial adapter units, this abutment face being arranged on one of the two partial adapter units, from a first condition, in which the abutment face is blocked against axial movement in relation to the suction ring portion, and into a second condition, in which it has axial play in relation to the suction ring portion; creating a vacuum to keep the two partial adapter units in the second relative position.

BRIEF DESCRIPTION OF THE DRAWINGS

Embodiments of the present invention will be explained below in greater detail with reference to the accompanying drawings, in which:

FIG. 1 shows schematically several components of an exemplary embodiment of an eye laser apparatus for laser creation of cuts in eye tissue, FIG. 2 shows an exploded perspective diagram of a patient adapter according to one exemplary embodiment, FIG. 3 shows a suction ring member and an auxiliary member of the patient adapter according to FIG. 2 in an assembled state, FIG. 4 shows the auxiliary member as well as a control ring of the patient adapter according to FIG. 2 in an assembled state, FIG. 5 shows the control ring according to FIG. 4 in an oblique view from above, FIGS. 6A to 6C show various positions of the control ring in relation to the auxiliary member, FIGS. 7A and 7B show a coupling of an applanation cone of the patient adapter according to FIG. 2 with the auxiliary member having axial play, FIGS. 8A and 8B show different states of the patient adapter according to FIG. 2, which correspond to a first relative position and a second relative position of two partial adapter units of the patient adapter to one another.

DETAILED DESCRIPTION OF THE DRAWINGS

Figure 8A:
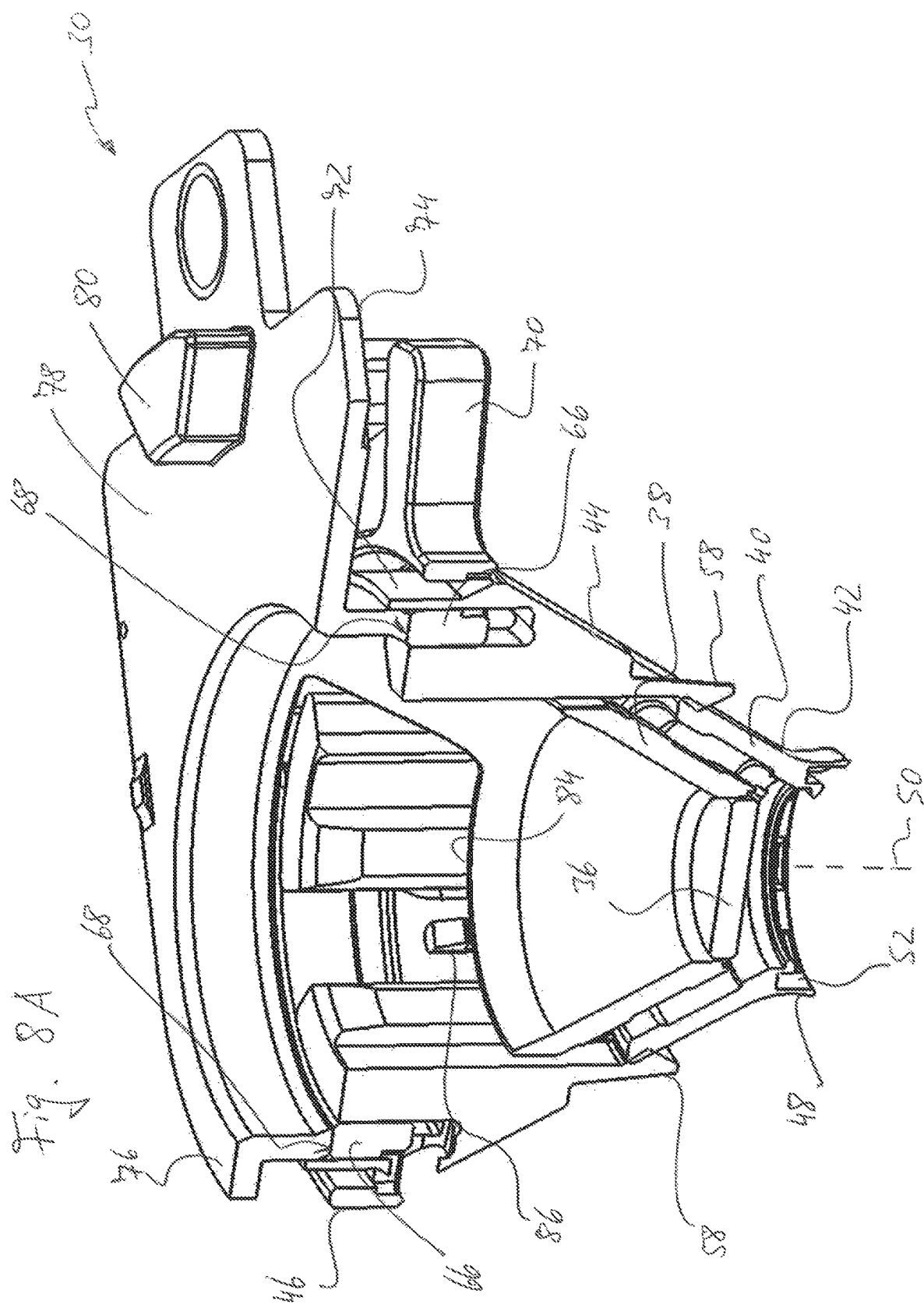

Reference is made first to FIG. 1. The eye laser apparatus shown in a schematic block diagram there is labeled as 10 in general. It serves to create cuts in a human eye 12 by means of a laser beam; such cuts are required as part of an intracorneal lenticular extraction, for example. The eye laser apparatus 10 comprises a laser source 14, which generates a beam 16 of ultrashort-pulse laser radiation. The term "ultra-short-pulse" is understood here to refer to pulse durations in the attosecond, femtosecond or picosecond range or, under some circumstances, in the nanosecond range, if other beam parameters have been selected suitably to create a photodisruption based on a laser-induced optical breakdown (LIOB) deep in the tissue of the eye. The wavelength of the laser beam 16 is in a UV range above approx. 300 nm, for example, or in an infrared range, for example, between approx. 800 nm and 1300 nm, so that transmission of the radiation into the eye tissue is ensured.

In the exemplary case shown here, the eye laser apparatus 10 also comprises a beam-widening unit 18 formed by a Galileo telescope, for example, that enlarges the beam diameter, a controllable deflector unit 20 (scanner) and a focusing objective 22 for focusing the beam. A stationary beam deflection mirror 24 arranged in the path of the beam between the scanner 20 and the focusing objective 22 is shown in FIG. 1 merely for the sake of the drawing but it need not be provided in a practical embodiment.

A program-controlled control unit 26 controls the laser source 14 and the scanner 20 in accordance with control commands contained in a control program 28. The control commands define a plurality of shot positions for the laser beam 16, which together represent a cutting pattern to be created in the eye 12. Each shot position represents a point in an xyz-coordinate system of the eye laser apparatus 10, whose z-axis runs along the direction of the laser beam 16 at the site where the beam exits from the focusing objective 22, and whose x and y-axes span a plane orthogonal to the z-axis. The control unit 26 controls the scanner 20 in such a way that, for each shot position predefined by the control program 28, the beam focus (i.e., the smallest beam diameter of the focused beam output by the focusing objective 22) is located at the respective point in the xyz-coordinate system.

The eye laser apparatus 10 delivers, to the eye tissue to be treated, one or more radiation pulses per shot position, depending on whether the radiation parameters are set for a single pulse application (i.e., a single beam pulse is enough to create photodisruption) or a multipulse application (i.e., multiple radiation pulses are necessary to create a photodisruption).

To adjust the beam focus in the x-direction and in the y-direction, the scanner 20 may comprise, for example, a pair of galvanometrically driven scanner mirrors, which are arranged so that they can be tilted about mutually orthogonal axes of rotation. For controlling the position of the beam focus in the z-direction, the eye laser apparatus 10 may comprise, for example, a suitable element to influence the divergence of the laser beam 16 before it enters the focusing objective 22. To do so, for example, a lens, which is adjustable in the direction of the beam, a lens of a variable refractive power or a hollow mirror of a variable curvature may be provided. From a structural standpoint, such elements may be part of the beam-widening unit 18. It is conceivable, for example, to design an entrance lens, which is itself designed as a divergent lens, of the beam-widening unit 18 to be adjustable with regard to its position and/or refractive power. Separate diagrams of the beam-widening unit 18 and of the scanner 20 in FIG. 1 serve only the purpose of illustrating the functional components of the eye laser apparatus 10 without having to stipulate a certain sequence of different structural components of the eye laser apparatus 10.

A patient adapter, labeled as 30 in general, serves to accurately position the eye 12 with respect to the eye laser apparatus 10 and is made up of a first partial adapter unit 32 and a second partial adapter unit 34. The patient adapter 30 is a disposable item, for example, which is used only once and then is either discarded after an operation or is sent to a sterilization station where it is sterilized for possible reuse. The first adapter unit 32 is placed on the eye 12 and affixed there by means of a vacuum. The second adapter unit 34 is designed for releasable coupling with the focusing objective 22 and carries an eye contact element 36, which is transparent, allowing the radiation of the laser beam 16 to permeate it, and offers a supporting surface for the eye 12 on its bottom side, which faces the eye 12. In the exemplary case shown here the eye contact element 36 is formed by an applanation plate which is designed to be flat on the side facing the eye as well as on the side facing away from the eye. In other embodiments, the eye contact element 36 may have, for example, a concave, convex or otherwise curved supporting surface for the eye 12, for example.

The second partial adapter unit 34 has a conically tapering section 38, which is inserted into a funnel section 40 of the first partial adapter unit 32. Due to this engagement of the conical section 38 in the funnel section 40, the first partial adapter unit 32 is centered with respect to the second partial adapter unit 34, i.e., is aligned in the x-direction and in the y-direction. In the z-direction, the first partial adapter unit 32 is coupled with the second partial adapter unit 34 by means of mechanical coupling members (not shown in detail in FIG. 1). The z-direction is also referred to below as the axial direction because in the assembled state illustrated in FIG.

1, in which the patient adapter 30 is coupled with the focusing objective 22, a ring axis defined by the first partial adapter unit 32 coincides with the z-axis. The above-mentioned coupling members, which act between the first partial adapter unit 32 and the second partial adapter unit 34, allow an axial adjustment of the two partial adapter units 32, 34 in relation to one another in a condition in which the two partial adapter units 32, 34 are joined together to form a module.

For additional details of an exemplary embodiment of the patient adapter 30, reference is now made to the following figures.

FIG. 2 shows that, in the exemplary embodiment considered here, the first partial adapter unit 32 is made up of a plurality of components manufactured separately and pre-assembled to form a unit. These components comprise a suction ring member 42, an auxiliary member 44 and a control ring 46. The suction ring member 42 forms the funnel section 40 and also has a suction ring portion 48 with a ring axis 50. The suction ring portion 48 forms a suction region 52 (see FIG. 3, for example), which is sealed when the suction ring portion 48 is placed on the eye 12 and is connected to one of two evacuating connections 54, 56 formed on the suction ring member 42. Hose lines, which are not shown in greater detail in the drawings, may be attached to the evacuation connections 54, 56 and lead to a vacuum source. The suction ring member 42 can be affixed on the eye 12 by means of a vacuum in the suction region 52.

The suction ring member 42 may be of a conventional design, for example.

In the exemplary case shown here, the auxiliary member 44 has a plurality of elastically deflectable snap-in tongues 58 by means of which the auxiliary member 44 can be snapped onto the suction ring member 42, specifically its funnel section 40. An axially stationary connection of the auxiliary member 44 to the suction ring member 42 is made possible by the snap-in tongues 58.

The auxiliary member 44 has a plurality of guide recesses 60 (four in this case) distributed over its circumference (the circumferential direction is defined with respect to the ring axis 50), each guide recess serving to engage a web 62 provided on the control ring 46. The webs 62 can be seen best in FIG. 5. They serve as connecting webs between an outer ring 64 of the control ring 46 and two diametrically opposed (based on the ring axis 50) supporting wall parts 66 situated radially inside the outer ring 64. The supporting wall parts 66 each form an axial stop surface 68 for the second partial adapter unit 34 on their side facing away from the eye. A gripping protrusion 70 extending radially away from the outer ring 64 allows simple manual operation of the control ring 46.

The guide recesses 60 are formed in a lateral wall 72 of the auxiliary member 44, such that the wall runs in a ring shape around the ring axis 50. The control ring 46 is placed on the auxiliary member 44 from the axial side facing away from the eye with the lateral wall 72 coming to lie between the outer ring 64 and the supporting wall parts 68 of the control ring 46. The guide recesses 60 are designed as slots, which pass through the entire wall thickness of the lateral wall 72. Each of the guide recesses 60 is comprised of three slot sections 74, 76, 78. Reference is now made in this regard to FIGS. 6A to 6C, in which, for reasons of simplicity, the outer ring 64 of the control ring 46 has been omitted, and only the supporting wall parts 66 and the connecting webs 62 are discernible. The above-mentioned slot sections 74, 76, 78 are shown on one of the guide recesses 60 in FIGS. 6A to 6C. The other guide recesses 60 have an identical shape in the exemplary case shown here.

The slot section 74 extends in the axial direction (based on the ring axis 50) and passes through to the axial edge of the lateral wall 72 facing away from the eye. In this way, the connecting webs 62 may be inserted axially into the slot sections 74 of the guide recesses 60—when the control ring 46 is placed on the auxiliary member 44.

The slot section 76 extends transverse to the slot section 74 and has an axial height, which corresponds essentially to the axial thickness of the connecting webs 62. When the connecting webs 62 are located in the region of the slot sections 76, there is thus a largely clearance-free coupling axially between the control ring 46 and the auxiliary member 44.

The slot section 78 again extends in the axial direction (like the slot section 74) and is adjacent to the end of the slot section 76, which is situated at a distance from the end of the slot section 76 adjacent to the slot section 74. The connecting webs 62 can move up and down axially in the slot sections 78, i.e., they have axial clearance there.

For assembly of the first partial adapter unit 32, the control ring 46 is placed on the auxiliary member 44 axially from the side thereof facing away from the eye. The radial connecting webs 62 of the control ring 46 are thereby inserted first into the slot sections 74 of the auxiliary member 44 in which these connecting webs slide downward axially until they reach the axial region of the slot sections 76. Then the control ring 46 and the auxiliary member 44 are rotated in relation to one another to move the connecting webs 62 into the slot sections 76. This situation is illustrated in FIG. 6A. An unintentional relative reverse rotation of the control ring 46 with respect to the auxiliary member 44 can be prevented by a local constriction in the slot, for example, in the transitional region between the slot section 74 and the slot section 76 of each guide recess 60. The control ring 46 and the auxiliary member 44 assume the relative positions according to FIG. 6A, in a condition when the patient adapter 30 is coupled to the focusing objective 22 of the laser apparatus 10 and the patient's eye is brought into proximity of the patient adapter 30.

The control ring 46 and the auxiliary member 44 can be transferred out of the relative position shown in FIG. 6A and into the state shown in FIG. 6B by turning the control ring 46 further in the same relative direction of rotation. In this state, the connecting webs 62 have come out of the slot sections 76 into the slot sections 78. A local slot constriction may also be formed at the transition from the slot section 76 to the slot section 78 of each guide recess 60 to prevent the control ring 46 from being unintentionally rotated back out of the position according to FIG. 6B and into the position according to FIG. 6A. In the situation according to FIG. 6B, the control ring 46 is situated essentially in the same position axially in relation to the auxiliary member 44 as in the situation according to FIG. 6A. However, the axial extent of the slot sections 78 allows the control ring 46 an axial movement clearance in relation to the auxiliary member 44, i.e., the control ring 46 can be inserted further axially into the auxiliary member 44. The result is shown in FIG. 6C, where the connecting webs 62 have slipped axially downward in the slot sections 78, to such an extent that they are in contact with the bottom of the slot sections 78 axially.

No further explanation is needed other than that the axial abutment faces 68 formed by the supporting wall parts 66 of the control ring 44 move equally downward axially when the control ring 46 slips downward axially from the position according to FIG. 6B into the position according to FIG. 6C.

With another glance at FIG. 2, the second partial adapter unit 34 is formed by a single component 74, which is referred to below simply as an applanation cone that is designed with the conical section 38 and carries a radially protruding collar 76, by means of which the applanation cone 74 can be inserted radially into an insert, which is provided on the focusing objective 22 of the laser apparatus 10 but is not shown in greater detail in the drawings, and in this way it can be coupled to the focusing objective without axial clearance. The collar 76 becomes wider in a partial region of the circumference of the cone to form a gripping plate 78, which facilitates manual handling of the applanation cone 74. A protrusion 80 provided on the gripping plate 78 serves as an abutment element to limit the radial depth of insertion of the applanation cone 74 into the aforementioned insert in the focusing objective 22.

A plurality of passages 84 (two in the exemplary case shown here) are provided in the conical jacket of the applanation cone 74, labeled as 82, in which snap-in tongues 86 provided on the auxiliary member 44 engage (see FIGS. 7A, 7B, 8A and 8B) to couple the applanation cone 74 with the auxiliary member 44. On the whole, two snap-in tongues 86 are provided on the auxiliary member 44 in the exemplary case shown here, namely one each in allocation to each of the passages 84.

The applanation cone 74 may be of a conventional design, for example.

Reference is now additionally made to FIGS. 7A and 7B. These show the applanation cone 74 and the auxiliary member 44 in a condition in which the two of them are coupled to one another, in that the snap-in tongues 86 engage in the passages 84. In assembly, the applanation cone 74 is placed on the auxiliary member 44 axially from above (after the auxiliary member has been assembled with the control ring 46), such that the snap-in tongues 86 slip along the outside circumferential surface of the conical section 38 and are deflected by the conical section 38 until they snap into the passages 84 in the applanation cone 74.

By comparing FIGS. 7A and 7B it can be seen that the coupling of the applanation cone 74 with the auxiliary member 44 has an axial clearance. Locking noses formed on the snap-in tongues 86 in FIG. 7A are in contact with the lower edge of the passages 84 axially. This is the top position axially of the applanation cone 74 in relation to the auxiliary member 44. In FIG. 7B, however, the applanation cone 74 has been shifted downward in relation to the auxiliary member 44 by an axial distance d. In this condition, the applanation cone 74 with its collar 76 is in contact with the upper end axially of the lateral wall 72 of the auxiliary member 44. The dimension d indicated in FIG. 7B thus represents the axial movement clearance of the applanation cone 74 in relation to the auxiliary member 44 (omitting the control ring 46 and the suction ring member 42).

Reference is now also made to FIGS. 8A and 8B, which show the patient adapter 30 in a completely assembled condition, wherein FIG. 8A corresponds to a first relative position of the two partial adapter units 32, 34 and FIG. 8B corresponds to a second relative position. In the first relative position according to FIG. 8A, the control ring 46 is in the rotational position according to FIG. 6A. The applanation cone 74 in this situation has its upper edge of its passages 84 in contact with the axial abutment faces 68, which are formed on the supporting wall parts 66 of the control ring 46. In the first relative position according to FIG. 8A, the axial position of the applanation cone 74 in relation to the auxiliary member 44 may correspond to the relative position of the two components 44, 74 shown in FIG. 7A. Alternatively, in the first relative position according to FIG. 8A, there is already a small axial interspace between the locking noses of the snap-in tongues 86 and the lower edge of the passages 84. In any case, in the first relative position according to FIG. 8A, the applanation plate 36 is in an axial position with respect to the suction ring member 42, which ensures that the applanation plate 36 is not yet in contact with the surface of the eye when the patient adapter 30 is affixed on the patient's eye by evacuation of the suction region 52 in the relative position shown in FIG. 8A.

After the eye has been affixed on the patient adapter 30, the control ring 46 is rotated manually by the surgeon or the surgeon's assistant into the rotational position according to FIG. 6B in relation to the auxiliary member 44, starting from the situation according to FIG. 8A. Because of the axial play of the connecting webs 62 of the control ring 46 in the slot sections 78 of the auxiliary member 44, there is the possibility of axial subsidence of the control ring 46 in relation to the auxiliary member 44 and the suction ring member 42—and therefore this also applies to the applanation cone 74. Axial subsidence here means that the conical section 38 of the applanation cone 74 is inserted further into the funnel section 40 of the suction ring member 42. This axial subsidence can be accomplished by the surgeon, for example, by an active axial approach of the focusing objective 22, which is carrying the patient adapter 30, to the eye of a patient, who is typically lying on a bed.

In the course of the axial subsidence, the applanation plate 36 approaches the surface of the eye more closely, then touches it and ultimately shapes it. The second relative position according to FIG. 8B corresponds to the condition in which the applanation cone 74 is inserted to the maximum depth into the suction ring member 42 (more precisely, into its funnel section 40). In this condition, the conical section 38 with its outer circumferential surface is in contact with the inside circumferential surface of the funnel section 40. A suction chamber 88 running peripherally in a ring shape, for example, is delimited between these two circumferential surfaces and can be evacuated through the other one of the two evaluation connections 54, 56. By creating a vacuum in the suction chamber 88, the two partial adapter units 32, 34 can be kept in the condition according to FIG. 8B. The evacuation of the suction chamber 88 can begin according to one embodiment after reaching the second relative position of the two partial adapter units 32, 34 according to FIG. 8B. According to another embodiment, evacuation of the suction chamber 88 (which may then not yet be closed all the way around) can be started already during the axial subsidence of the applanation cone 74 in relation to the auxiliary member 44 and the suction ring member 42, or the axial subsidence may be accomplished merely by evacuation of the suction chamber 88.

The patient adapter 30 is suitable for, but is not limited to, application cases in which the most accurate possible alignment of a reference axis of the patient's eye with an optical axis of the laser apparatus is desired.

The invention claimed is:

1. A patient adapter for an eye laser apparatus, comprising:
   a first partial adapter unit comprising:
   a suction ring member comprising a suction ring portion configured to be affixed to an eye by means of suction force, the suction ring portion having an annular portion that defines a ring axis, the ring axis passing through the center of the annular portion, the ring axis substantially perpendicular to the annular portion; and
   an auxiliary member formed separately from and coupled to the suction ring member;

a second partial adapter unit formed separately from the first partial adapter unit, the second partial adapter unit configured to be releasably coupled to the eye laser apparatus and comprising an eye contact element for shaping a surface of the eye; and a control member formed separately from the first and second partial adapter units, the control member guided on the auxiliary member for movement relative thereto, the control member configured to be adjusted between a first control position and a second control position, the control member comprising a control ring arranged to rotate about the ring axis in a plane generally parallel to a plane containing the annular portion of the suction ring, the first control position being a first rotational position, the second control position being a second rotational position, wherein:

the first and second partial adapter units are configured to be adjusted with respect to each other between a first relative position in which the eye contact element assumes a first axial position with respect to the suction ring portion and a second relative position in which the eye contact element assumes a second axial position with respect to the suction ring portion;

one of the first and second partial adapter units comprises an axially displaceable abutment face configured to abut with the other of the first and second partial adapter units, the abutment face comprising an axially facing end face of the control member; and the control member in the first control position prohibits axial displacement of the abutment face of the one of the first and second partial adapter units, and in the second control position permits substantially only axial displacement of the abutment face towards the auxiliary member;

wherein the control ring comprises an outer ring and a web connecting a wall part to the outer ring, such that rotation of the control ring causes the web to engage a slot section in the auxiliary member thereby permitting axial motion of the control ring relative to the auxiliary member.

2. The patient adapter of claim 1, wherein:
the first axial position of the eye contact element corresponds to a position in which the eye contact element is out of contact with the eye when the suction ring portion is on the eye; and
the second axial position of the eye contact element corresponds to a position in which the eye contact element is in shaping contact with the eye when the suction ring portion is on the eye.

3. The patient adapter of claim 1, wherein:
at least one of the first and second partial adapter units comprises a system of one or more snap-in tongues; and
the one or more snap-in tongues are configured to couple the first and second partial adapter units to each other with an axial clearance.

4. The patient adapter of claim 1, wherein the abutment face is on the first partial adapter unit.

5. The patient adapter of claim 1, wherein:
the first rotational position of the control ring corresponds to an axial position of the eye contact element in which the eye contact element is out of contact with the eye when the suction ring portion is on the eye; and
in the second rotational position the axial play permits the control ring to move into an axial position where an axial position of the eye contact element is in shaping contact with the eye.

6. The patient adapter of claim 5, wherein:
the control ring includes a guided member configured to be guided into a guide recess in one of the first and second partial adapter units; and
an engagement of the guided member into the guide recess is substantially without axial clearance in the first rotational position of the control ring and has an axial play in the second rotational position.

7. The patient adapter of claim 1, wherein:
the control ring includes a radially protruding gripping protrusion for rotatory manual manipulation of the control ring.

8. The patient adapter of claim 1, wherein:
at least one of the suction ring member and the auxiliary member comprises a system of one or more snap-in tongues; and
the one or more snap-in tongues are configured to couple the auxiliary member to the suction ring member without axial clearance.

9. The patient adapter of claim 1, wherein:
the first partial adapter unit comprises a centering portion that tapers in a funnel-type manner in a direction axially toward the suction ring portion;
the second partial adapter unit comprises a conical portion adapted for axial insertion into the centering portion; and
the conical portion is configured to be inserted deeper into the centering portion in the second relative position of the first and second partial adapter units than in the first relative position.

10. The patient adapter of claim 9, comprising:
a suction chamber that is at least partially delimited by the first and second partial adapter units, the suction chamber between the centering portion and the conical portion, whereby the eye contact element can be held in the second axial position relative to the suction ring portion by evacuation of the suction chamber.

11. The patient adapter of claim 1, wherein:
the one of the first and second partial adapter units that comprises the axially displaceable abutment face comprises a plurality of abutment faces for axial abutment of the other of the first and second partial adapter units; and
the plurality of abutment faces are distributed in a circumferential direction around the ring axis.

* * * * *